(12) United States Patent
West et al.

(10) Patent No.: US 7,442,395 B2
(45) Date of Patent: *Oct. 28, 2008

(54) **FORMULATION FOR TREATING CANDIDIASIS USING *MORINDA CITRIFOLIA***

(75) Inventors: Brett West, Orem, UT (US); Claude Jarakae Jensen, Cedar Hills, UT (US); Afa Kehaati Palu, American Fork, UT (US); Robert Ogden, Cedar Hills, UT (US); Scott Gerson, Brewster, NY (US)

(73) Assignee: Tahitian Noni International, Inc., Provo, UT (US)

( * ) Notice: Subject to any disclaimer, the term of this patent is extended or adjusted under 35 U.S.C. 154(b) by 8 days.

This patent is subject to a terminal disclaimer.

(21) Appl. No.: 11/339,071

(22) Filed: Jan. 26, 2006

(65) Prior Publication Data

US 2006/0159788 A1   Jul. 20, 2006

(51) Int. Cl.
*A61K 36/00* (2006.01)
(52) U.S. Cl. ........................ 424/777; 424/725
(58) Field of Classification Search ........................ None
See application file for complete search history.

(56) References Cited

U.S. PATENT DOCUMENTS

| | | |
|---|---|---|
| 4,039,559 A | 8/1977 | Nakamura |
| 4,409,144 A | 10/1983 | Heinicke |
| 4,463,025 A | 7/1984 | Strobel |
| 4,543,212 A | 9/1985 | Heinicke |
| 4,666,606 A | 5/1987 | Heinicke et al. |
| 4,793,991 A | 12/1988 | Slimak |
| 4,948,785 A | 8/1990 | Nguyen |
| 4,996,051 A | 2/1991 | Meer et al. |
| 5,106,634 A | 4/1992 | Thacker et al. |
| 5,110,803 A | 5/1992 | Nguyen |
| 5,213,836 A | 5/1993 | McGillivray et al. |
| 5,268,467 A | 12/1993 | Verbiscar |
| 5,275,834 A | 1/1994 | Thibault et al. |
| 5,288,491 A | 2/1994 | Moniz |
| 5,431,927 A | 7/1995 | Hand et al. |
| 5,472,699 A | 12/1995 | Duffy et al. |
| 5,503,825 A | 4/1996 | Lane |
| 5,595,756 A | 1/1997 | Bally et al. |
| 5,616,569 A | 4/1997 | Reinhart |
| 5,717,860 A | 2/1998 | Graber et al. |
| 5,725,875 A | 3/1998 | Noll et al. |
| 5,736,174 A | 4/1998 | Cooper et al. |
| 5,744,187 A | 4/1998 | Gaynor |
| 5,770,217 A | 6/1998 | Kutilek, III et al. |
| 5,776,441 A | 7/1998 | Scancarella et al. |
| 5,843,499 A | 12/1998 | Moreau et al. |
| 5,851,573 A | 12/1998 | Lepine et al. |
| 5,922,766 A | 7/1999 | Acosta et al. |
| 5,961,998 A | 10/1999 | Arnaud et al. |
| 5,962,043 A | 10/1999 | Jones et al. |
| 5,976,549 A | 11/1999 | Lewandowski |
| 6,029,141 A | 2/2000 | Bezos et al. |
| 6,039,952 A | 3/2000 | Sunvold et al. |
| 6,086,859 A | 7/2000 | Calello et al. |
| 6,086,910 A | 7/2000 | Howard et al. |
| 6,133,323 A | 10/2000 | Hayek |
| 6,136,301 A | 10/2000 | Pelle et al. |
| 6,139,897 A | 10/2000 | Goto et al. |
| 6,156,355 A | 12/2000 | Shields, Jr. et al. |
| 6,214,351 B1 | 4/2001 | Wadsworth et al. |
| 6,254,913 B1 | 7/2001 | Wadsworth et al. |
| 6,261,566 B1 | 7/2001 | Pillai et al. |
| 6,280,751 B1 | 8/2001 | Fletcher et al. |
| 6,291,533 B1 | 9/2001 | Fleischner |
| 6,299,925 B1 | 10/2001 | Xiong et al. |
| 6,387,370 B1 | 5/2002 | Yegorva |
| 6,405,948 B1 | 6/2002 | Hahn et al. |
| 6,417,157 B1 | 7/2002 | Wadsworth et al. |
| 6,436,449 B2 | 8/2002 | Gidlund |
| 6,477,509 B1 | 11/2002 | Hammons et al. |
| 6,528,106 B2 | 3/2003 | Wadsworth et al. |
| 6,589,514 B2 | 7/2003 | Jensen et al. |
| 6,737,089 B2 | 5/2004 | Wadsworth et al. |
| 6,749,875 B2 | 6/2004 | Selleck |
| 6,855,345 B2 | 2/2005 | Jensen et al. |
| 6,855,354 B2 | 2/2005 | Jensen et al. |
| 7,014,873 B2 | 3/2006 | West et al. |
| 7,018,662 B2 | 3/2006 | Jensen et al. |
| 7,048,952 B2 * | 5/2006 | Gerson et al. ................ 424/725 |

(Continued)

FOREIGN PATENT DOCUMENTS

JP         11-43442         10/1989

(Continued)

OTHER PUBLICATIONS

Starbuck, J.D. Elderberry & Cat's Claw; Better Nutrition; Sep. 1998; 60, 9, pp. 54, 55, 56 & 58.*
Product Alert: Tahiti Trader's Noni Juice—Ready to Drink Coctail; High Potency Dietary Supplement; Jun. 2000, vol. 30, No. 11, one page.*
Drug Development; The Pain Killer Tree: An Ancient Remedy Rediscovered; Pain & Central Nervous System Week, Nov. 2001pp. 1-2.*
Rosenfeld, M Tropical Noni, A Tonic Boom; Nasty-Tasting Fruit Rockets Onto the Health Product Market; The Washington Post, Aug. 1997, p. C01 (pp. 1-4 of ProQuest).*

(Continued)

*Primary Examiner*—Patricia Leith
(74) *Attorney, Agent, or Firm*—Kirton & McConkie; Michael F. Krieger

(57) ABSTRACT

The present invention features a formulation from the Indian mulberry plant (*Morinda citrifolia*) comprising *Morinda citrifolia* fruit juice, *Morinda citrifolia* oil, quercetin, *Morinda citrifolia* puree juice and *Morinda citrifolia* dietary fiber treating Candidiasis.

13 Claims, No Drawings

U.S. PATENT DOCUMENTS

| | | | |
|---|---|---|---|
| 2001/0033871 | A1 | 10/2001 | Gidlund |
| 2002/0068102 | A1 | 6/2002 | Su et al. |
| 2002/0090406 | A1 | 7/2002 | Su et al. |
| 2002/0147643 | A1 | 10/2002 | Olsen et al. |
| 2002/0187168 | A1 | 12/2002 | Jensen et al. |
| 2003/0060405 | A1 | 3/2003 | Klieiman et al. |
| 2003/0086989 | A1 | 5/2003 | Jensen et al. |
| 2003/0086990 | A1 | 5/2003 | Wang et al. |
| 2003/0108629 | A1 | 6/2003 | Chou |
| 2003/0108630 | A1 | 6/2003 | Story et al. |
| 2003/0108631 | A1 | 6/2003 | Jensen et al. |
| 2003/0134001 | A1 | 7/2003 | Jensen et al. |
| 2003/0134002 | A1 | 7/2003 | Jensen et al. |
| 2003/0206895 | A1 | 11/2003 | Cavazza |
| 2003/0225005 | A1 | 12/2003 | Gerson et al. |
| 2004/0258780 | A1 | 12/2004 | Woltering et al. |

FOREIGN PATENT DOCUMENTS

| | | |
|---|---|---|
| WO | 88/05304 A1 | 7/1988 |
| WO | 01/15551 A1 | 3/2001 |
| WO | 01/15553 A1 | 3/2001 |
| WO | 01/64231 A | 9/2001 |
| WO | 02/45654 A | 6/2002 |
| WO | 02/45734 A | 6/2002 |

OTHER PUBLICATIONS

Drug Development; The Pain Killer Tree: An Ancient Remedy Rediscovered; Pain & central Nervous System Week; Atlanta, Nov. 19, 2001; p. 19 (pp. 1-2 of ProQuest).*
Daulataba et al., "Ricinoleic acid in *Morinda citrifolia* seed oil," J. Oil Tech. Assoc. India (Mumbai, India) 21(2):26-27 (1989).
Dittmar, Morinda, "Use in Indigenous Samoan Medicine," J. of Herbs, Spices & Medicinal Plants, 1(3):77-92 (1993).
El-Gammal et al., "Antimicrobial Activities of Some Flavonoid Compounds," Microbiol. 141:561-565 (1986).
Elkins, Hawaiian Noni, Woodland Publishing, pp. 6-31 (1998).
Farine et al., Volatile Components of Ripe Fruits of??.
Fisher, Living Better, V 1(5).
Gagnon, D., "Liquid Herbal Drops in Everyday Use," 3d Ed., Bot. Res. Ed. Inst., p. 27 (1997)
Gura, "Systems for Identifying New Drugs are Ofter Faulty," Science 278:1041-1042 (1997).
Hawegawa et al., "Anti-Helicobacter Pylor; Medicine Containing Extract of Dried Root of *Morinda citrifolia*," Abstract (1996).
Hirazumi et al.,"An Immunomodulatory Polysaccharide-Rich Substance from the Fruit Juice of *Morina citrifolia*(Noni)withAntitumorActivity,"Phytotherapy Research, 13:380-387(1999).
Holleran, "The Zotics Splash, Beverage Industry," 91(6) (2000).
Lampur, "Morinda achieves phenomenal sales of Tahitian noni juice", Malaysian Nat. News Agency Jul. 1999, p. 1.
Kimstra et al., "Foods of the Key deer," FL Sci., 53(4):264-273 (1990).
Lane, "The Merck Manual," 17th Ed., pp. 449-451 (1999) *** Need Copy.
Levand et al., "Some chemical constituents of *Morinda citrifolia*," Planta Medica 36(2):186-187 (1979).
Liu et al,2 Novel GlycosidesfromtheFruitsofMorindaCitrifolia (Noni) Inhibit AP-1 Transactivation &CellTransformationintheMouseEpidermalJB6CellLine, Cancer Res.61:5749-5756(2001.
Morona et al., "Pharmacological properties of some aminoalkanolic derivatives of xanthone," Pharmazie 56:567-572 (2001).
Morton, "The ocean-going noni, or Indian mulberry (*Morinda citrifolia*) and some of its 'colorful' relatives," Econ. Bot., 46(3):241-256 (192).
Mueller et al., "Noni Juice (*Morinda Citrifolia*): Hidden Potential for Hyperkalameia?" Am H. Kidney Diseases.
Mumford, L., "Benefits of Noni Juice may be Imagined; $30 Price Tag Isn't", So. Bend Tribune, So. Bend, Ind., pp. 1-2 (1998).
Naito, "Trace components in mulberry leaves," Nippon Nogei Kagaku Kaishi 42(7):423-425 (1968).
Peres et al., "Tetraoxygenated naturally occurring xanthones," Phytochemestry 55:683-710 (2000).
Product Alert. Oct. 11, 1999 29(19) PROMT Abstract.
Product Alert. Dec. 27, 1999 (29(24) PROMT Abstract.
Product Alert. Jun. 12, 2000 30(11) PROMT Abstract.
Rosenfelt, "Tropical Noni, a Tonic Boom; Nasty-Tasting Fruit Rockets onto the Health Product Market," Wash. Post; Aug. 7, 1997, p. C01:1-4 of Proquest.
Sang et al., "Chemical Components in Noni Fruits and Leaves (*Morinda citrifolia* L.); Quality Management of Nutraceuticals,"Proceedings of Symposium,ACS,Wash.,DC pp. 134-150(2002.
Sang et al., "Flavonal Glycosides and Novel Irdoid Glycoside from the Leaves of *Morinda citrifolia*," J. Agric.
"Rachel Perry Environmental Skin Protector SPF 18," Product Alert, V.29(2) (1999).
Tahitian Noni Products (http://www.noni-now.com) (1998-2003).
Termumo Copr., "Anti-helicobacter pylon agent confic. Extract of dried roots of *Morinda citrifolia*. . . " Database DWPI on West, An. 1996-439483 JP 08-217686-Japan (Aug. 1996).
Wang et al., J. Agric. Food Chem. 47(12):4880-7882 (1999).
Wang, Mingfu., "Chemical Components of Sage, Thyme and noni and their antioxidant and anticancer activities,".
Webb, "Noni Juice Advice," Prevention Magazine 52:66 (2000).
Website publication: "A Pure Hawaiian Noni Juice," web.archive. org/web/20030523122956/http://www.nonialoha.com (2003).
Website publication: "Betterman" by Interceuticals, www. naturalhealtheconsultant.com/Monographs/Betterman.html (1998).
Website publication: "Morinda," www.drugdigest.org/DD/DV/ HebsTake/0,3927,552025/Morinda.00.html (2003).
Website publication: "NONI in the News," www.incc.org/news-june. htm (2002).
Website publication: "NONI," www.web.archive.org/web/ 20020207214423/http://wwwlnukahivatrading.com/noni.htm (2002).
Website publication: "Noni Juice," www.tipsofallsorts.com/noni. html p. 1-11 (1999).
Website publication "Noni or Nonu Fruit," www.noni-nonu.com (1999).
Website publication "100% Pure Standardization Noni Juice," www. evitamins.com (1999).
Weil, A., "Alternatives," Northern Echo, Darlington, UK, p. 1-2 (2000).
Yamada et al., "Antibacterial Composition" Abstract (1984).
Younos et al., "Analgesic and Behavioural Effects of *Morinda-citrifolia*" Planta Medica 56(5):430-434 (1990).

* cited by examiner

FORMULATION FOR TREATING CANDIDIASIS USING *MORINDA CITRIFOLIA*

RELATED APPLICATIONS

This application claims priority to U.S. Pat. Ser. No. 10/294,089, dated Nov. 14, 2002, "Method and Formulation for Treating Candidiasis Using *Morinda Citrifolia*", and claims priority to U.S. Provisional Application No. 60/331, 504, filed Nov. 14, 2001, entitled, "Method and Formulation for Treating Candidiasis Using *Morinda Citrifolia* Juice."

BACKGROUND

1. Field of the Invention

The present invention is directed toward methods and formulations for treating Candidiasis, and particularly towards various methods and naturaceutical formulations, compositions, and substances comprising *Morinda citrifolia* for inhibiting, blocking, and preventing the overgrowth of *Candida albicans* in mammals.

2. Background of the Invention

There exists in the body literally billions of microorganisms that function to assist in everyday maintenance and development. This normal resident microbial population includes potential pathogens as well as organisms that help to keep the potential pathogens in check.

Microorganisms *Candida albicans,* and other strains of *Candida,* are yeast or yeast-like fungi that are capable of growing on and within the human body and that normally or naturally inhabit our digestive system: the mouth, throat, intestines and genitourinary tract. *Candida* is a normal part of the bowel flora (the organisms that naturally live inside our intestines, and are not parasitic). It has many functions inside our digestive tract, one of them which is to recognize and destroy harmful bacteria. Without *Candida albicans* in our intestines we would be defenseless against many pathogenic bacteria. Under normal circumstances, a healthy individual can have millions of *Candida albicans* in their system.

Our immune system is supposed to keep these organisms under control, together with various strains of friendly bacteria, such as *Lactobacillus acidophilus, B. bifidum, Lactobacillus bulgaricus, S. thermophilus,* and *L. salivarius.* However, if the number of friendly bacteria is decreased (e.g., as a result of antibiotics, pesticides, chlorine, etc.) in relation to the number of *Candida,* the immune system is weakened and other conditions for yeast proliferation occur (e.g., improper pH in the digestive system, or high sugar diet). *Candida albicans* will shift from yeast to a mycelial fungal form and start to invade the body. In the yeast state *Candida* is a non-invasive, sugar-fermenting organism, while in the fungal state it is invasive and can produce rhizoids, which are very long root-like structures. Rhizoids can penetrate mucosa or intestinal walls, leaving microscopic holes and allowing toxins, undigested food particles and bacteria and yeast to enter the bloodstream.

Certain physiological environmental conditions can promote the overgrowth of the fungus in particular areas of the body. For example, the fungus may proliferate excessively in the mouth resulting in a condition known as thrush or may grow excessively in the genital area resulting in what is commonly referred to as a genital yeast infection.

Women are particularly susceptible to genital yeast infections, the symptoms of which include vaginal itching, burning, redness, and irritation of the vaginal area. Severe vaginal yeast infections may cause swelling of the vulva and result in inflammation of the urinary opening. Additionally, women may experience abnormal vaginal discharge. These symptoms can cause extreme discomfort, but are typically not life threatening. Other forms of Candidiasis (such as Hepatosplenic Candidiasis, which occurs in cancer and leukemia patients and endocardial Candidiasis) are more serious and require professional medical attention.

It is estimated that three out of four women will experience a genital yeast infection at some time in their lives. In some cases the yeast infection will be a recurring problem. Genital yeast infections also occur in men, but with much less frequency than with women. Consumers spend more than 60 million dollars each year in over-the-counter yeast infection remedies in attempts to relieve the symptoms of yeast infection or cure yeast infections. Present treatments include a number of over-the-counter creams and other topical medications that are placed directly on the infected area. Additionally, prescription oral medication and vaginal suppositories are also available to relieve and treat yeast infection.

The prior art treatments for yeast infections described above can be unpleasant and in some circumstances are not practical. Creams and topical lotions can be messy and uncomfortable and must be applied in private. In order to receive prescription medications, an infected person may have to endure the inconvenience of being examined by a doctor and having the prescription filled at a pharmacy. Suppository type treatments are considered by many to be undesirable. Another problem with the over-the-counter prior art treatments described above is that they fail to safeguard against the potential harm from improper use of the medication. It is reported that people experiencing the symptoms of yeast infections such as those described above will often self-diagnose themselves as having a yeast infection, when in fact they do not. Studies show that, more often than not, such self-diagnosis is incorrect. Thus, consumers buying over-the-counter medications for yeast infections may in fact be administering medications that are unnecessary or even harmful to them. A significant amount of money is spent on over the counter yeast infection treatments that do not work and can interfere with proper diagnosis of the condition.

It would be a significant advancement in the art to provide an improved method for treating Candidiasis and its symptoms. It would also be an advancement to reduce and inhibit the overgrowth of various microorganisms within the body, such as *Candida* fungus and specifically *Candida albicans.* Stated differently, it would be an advancement in the art to provide a natural formulation that exhibits significant antimicrobial activity within the body, or that inhibits and prevents the overgrowth of microorganisms within the body.

SUMMARY AND OBJECTS OF THE INVENTION

In accordance with the invention as embodied and broadly described herein, the present invention features a method for inducing antimicrobial and antifungal activity and inhibiting and preventing the overgrowth of *Candida* for the purpose of treating and preventing Candidiasis through the prophylactic administration of a naturaceutical formulation comprising at least one of a processed *Morinda citrifolia* product. The Processed *Morinda citrifolia* product may be in the form of fruit juice, puree juice, fruit or puree juice concentrate, oil extract, dietary fiber, or one of an alcohol or aqueous extract.

The naturaceutical formulation may be embodied in any form suitable for systemic internalization, namely orally, topically or transdermally, or intravenously. Moreover, the naturaceutical formulation may contain various amounts and concentrations of the processed *Morinda citrifolia* product, along with other various ingredients, such as a carrier medium or composition in a topical dermal naturaceutical formulation.

Though practically inedible in it's natural form, *Morinda citrifolia* can be processed and used within a naturaceutical formulation to treat or alleviate the symptoms of yeast infections and other related diseases or infections of Candidiasis.

Several experiments are presented herein that illustrate the treatment and preventative effects of *Morinda citrifolia* on the overgrowth of *Candida* and other related microorganisms.

The present invention further features a method for administering the *Morinda citrifolia*-based naturaceutical formulation concurrently with a pharmaceutical medication designed to treat and prevent Candidiasis. The naturaceutical formulation functions to increase the efficacy of such medications.

DETAILED DESCRIPTION OF THE PREFERRED EMBODIMENTS

It will be readily understood that the components of the present invention, as generally described herein, could be arranged and designed in a wide variety of different configurations. Thus, the following more detailed description of the embodiments of the system and method of the present invention is not intended to limit the scope of the invention, as claimed, but is merely representative of the presently preferred embodiments of the invention.

The present invention describes and features formulations and methods for treating Candidiasis and its related conditions through the prophylactic administration of a naturaceutical formulation or composition comprising one or more processed *Morinda citrifolia* products.

The presently preferred embodiments of the invention will be best understood by separating the description into sections, the first pertaining to a general discussion regarding *Morinda citrifolia,* including its origins, processing techniques, and health benefits, and the methods employed to produce and manufacture the processed *Morinda citrifolia* products used as key ingredients in the naturaceutical formulations described herein; and the second being a more detailed and specific discussion on the *Morinda citrifolia*-based methods and naturaceutical formulations or compositions used to treat and inhibit the growth of *candida albicans,* and to prevent such, as well as a method for treating and preventing Candidiasis and its associated symptoms or conditions, such treatment methods involving the prophylactic administration of the processed *Morinda citrifolia* product-based formulations as described herein. Examples of experimental studies and the results obtained are also provided herein.

General Discussion of *Morinda citrifolia* and the Methods used to Produce Processed *Morinda citrifolia* Products The Indian Mulberry or Noni plant, known scientifically as *Morinda citrifolia* L. (hereinafter "*Morinda citrifolia*"), is a shrub or small tree up to 10 m in height. The leaves are oppositely arranged with an elliptic to ovate form. The small white flowers are contained in a fleshy, globose, head-like cluster. The fruits are large, fleshy, and ovoid. At maturity, they are creamy-white and edible, but have an unpleasant taste and odor. The plant is native to Southeast Asia and has spread in early times to a vast area from India to eastern Polynesia. It grows randomly in the wild, and it has been cultivated in plantations and small individual growing plots. The *Morinda citrifolia* flowers are small, white, three to five lobed, tubular, fragrant, and about 1.25 cm long. The flowers develop into compound fruits composed of many small drupes fused into an ovoid, ellipsoid or roundish, lumpy body, with waxy, white, or greenish-white or yellowish, semi-translucent skin. The fruit contains "eyes" on its surface, similar to a potato. The fruit is juicy, bitter, dull-yellow or yellowish-white, and contains numerous red-brown, hard, oblong-triangular, winged 2-celled stones, each containing four seeds.

When fully ripe, the fruit has a pronounced odor like rancid cheese. Although the fruit has been eaten by several nationalities as food, the most common use of the *Morinda citrifolia* plant was as a red and yellow dye source. Recently, there has been an interest in the nutritional and health benefits of the *Morinda citrifolia* plant, further discussed below. Because the *Morinda citrifolia* fruit is for all practical purposes inedible, the fruit must be processed in order to make it palatable for human consumption and included in the naturaceuticals used to treat abd prevent the growth of *candida albicans* and Candidiasis.

Processed *Morinda citrifolia* fruit juice can be prepared by separating seeds and peels from the juice and pulp of a ripened *Morinda citrifolia* fruit; filtering the pulp from the juice; and packaging the juice. Alternatively, rather than packaging the juice, the juice can be immediately included as an ingredient in another food product, frozen or pasteurized. In some embodiments, the juice and pulp can be pureed into a homogenous blend to be mixed with other ingredients. Other process include freeze drying the fruit and juice. The fruit and juice can be reconstituted during production of the final juice product. Still other processes include air drying the fruit and juices, prior to being masticated.

The present invention utilizes the fruit juice, the puree, and the oil extracted from the *Morinda Citrifolia* plant. In a currently preferred process of producing *Morinda citrifolia* fruit juice, the fruit is either hand picked or picked by mechanical equipment. The fruit can be harvested when it is at least one inch (2-3 cm) and up to 12 inches (24-36 cm) in diameter. The fruit preferably has a color ranging from a dark green through a yellow-green up to a white color, and gradations of color in between. The fruit is thoroughly cleaned after harvesting and before any processing occurs.

The fruit is allowed to ripen or age from 0 to 14 days, with most fruit being held from 2 to 3 days. The fruit is ripened or aged by being placed on equipment so it does not contact the ground. It is preferably covered with a cloth or netting material during aging, but can be aged without being covered. When ready for further processing the fruit is light in color, from a light green, light yellow, white or translucent color. The fruit is inspected for spoilage or for excessively green color and hard firmness. Spoiled and hard green fruit is separated from the acceptable fruit.

The ripened and aged fruit is preferably placed in plastic lined containers for further processing and transport. The containers of aged fruit can be held from 0 to 30 days. Most fruit containers are held for 7 to 14 days before processing. The containers can optionally be stored under refrigerated conditions prior to further processing. The fruit is unpacked from the storage containers and is processed through a manual or mechanical separator. The seeds and peel are separated from the juice and pulp.

The juice and pulp can be packaged into containers for storage and transport. Alternatively, the juice and pulp can be immediately processed into a finished juice product. The containers can be stored in refrigerated, frozen, or room temperature conditions. The *Morinda citrifolia* juice and pulp are preferably blended in a homogenous blend, after which they may be mixed with other ingredients, such as flavorings, sweeteners, nutritional ingredients, botanicals, and colorings.

The finished juice product is preferably heated and pasteurized at a minimum temperature of 181° F. (83° C.) or higher up to 212° F. (100° C.).

Another product manufactured is *Morinda citrifolia* puree and puree juice, in either concentrate or diluted form. Puree is essentially the pulp a separated from the seeds and is different than the fruit juice product described herein.

Each product is filled and sealed into a final container of plastic, glass, or another suitable material that can withstand the processing temperatures. The containers are maintained at the filling temperature or may be cooled rapidly and then placed in a shipping container. The shipping containers are preferably wrapped with a material and in a manner to maintain or control the temperature of the product in the final containers.

The juice and pulp may be further processed by separating the pulp from the juice through filtering equipment. The filtering equipment may include a centrifuge decanter, a screen filter with a size from 1 micron up to 2000 microns, more preferably less than 500 microns, a filter press, reverse osmosis filtration., and any other standard commercial filtration devices. The operating filter pressure preferably ranges from 0.1 psig up to about 1000 psig. The flow rate preferably ranges from 0.1 g.p.m. up to 1000 g.p.m., and more preferably between 5 and 50 g.p.m. The wet pulp is washed and filtered at least once and up to 10 times to remove any juice from the pulp. The wet pulp typically has a fiber content of 10 to 40 percent by weight. The wet pulp may be pasteurized at a temperature of 181° F. (83° C.) minimum and then packed in drums for further processing or made into a high fiber product.

Drying may further process the wet pulp. The methods of drying may include freeze-drying, drum drying, tray drying, sun drying, and spray drying. The dried *Morinda citrifolia* pulp may include a moisture content in the range from 0.1 to 15 percent by weight and more preferably from 5 to 10 percent by weight. The dried pulp preferably has a fiber content in the range from 0.1 to 30 percent by weight, and more preferably from 5 to 15 percent by weight.

The high fiber product may include wet or dry *Morinda citrifolia* pulp, supplemental fiber ingredients, water, sweeteners, flavoring agents, coloring agents, and/or nutritional ingredients. The supplemental fiber ingredients may include plant based fiber products, either commercially available or developed privately. Examples of some typical fiber products are guar gum, gum arabic, soybean fiber, oat fiber, pea fiber, fig fiber, citrus pulp sacs, hydroxymethylcellulose, cellulose, seaweed, food grade lumber or wood pulp, hemicellulose, etc. Other supplemental fiber ingredients may be derived from grains or grain products. The concentrations of these other fiber raw materials typically range from 0 up to 30 percent, by weight, and more preferably from 10 to 30 percent by weight.

Typical sweeteners may include, but are not limited to, natural sugars derived from corn, sugar beet, sugar cane, potato, tapioca, or other starch-containing sources that can be chemically or enzymatically converted to crystalline chunks, powders, and/or syrups. Also sweeteners can consist of artificial or high intensity sweeteners, some of which are aspartame, sucralose, stevia, saccharin, etc. The concentration of sweeteners may be between from 0 to 50 percent by weight, of the formula, and more preferably between about 1 and 5 percent by weight.

Typical flavors can include, but are not limited to, artificial and/or natural flavor or ingredients that contribute to palatability. The concentration of flavors may range, for example, from 0 up to 15 percent by weight, of the formula. Colors may include food grade artificial or natural coloring agents having a concentration ranging from 0 up to 10 percent by weight, of the formula.

Typical nutritional ingredients may include vitamins, minerals, trace elements, herbs, botanical extracts, bioactive chemicals and compounds at concentrations from 0 up to 10 percent by weight. Examples of vitamins one can add to the fiber composition include, but are not limited to, vitamins A, B1 through B12, C, D, E, Folic Acid, Pantothenic Acid, Biotin, etc. Examples of minerals and trace elements one can add to the fiber composition include, but are not limited to, calcium, chromium, copper, cobalt, boron, magnesium, iron, selenium, manganese, molybdenum, potassium, iodine, zinc, phosphorus, etc. Herbs and botanical extracts include, but are not limited to, alfalfa grass, bee pollen, chlorella powder, Dong Quai powder, Ecchinacea root, Gingko Biloba extract, Horsetail herb, Indian mulberry, Shitake mushroom, spirulina seaweed, grape seed extract, etc. Typical bioactive chemicals may include, but are not limited to, caffeine, ephedrine, L-carnitine, creatine, lycopene, etc.

The juice and pulp can be dried using a variety of methods. The juice and pulp mixture can be pasteurized or enzymatically treated prior to drying. The enzymatic process begins with heating the product to a temperature between 75° F. and 135° F. It is then treated with either a single enzyme or a combination of enzymes. These enzymes include, but are not limited to, amylase, lipase, protease, cellulase, bromelin, etc. The juice and pulp may also be dried with other ingredients, such as those described above in connection with the high fiber product. The typical nutritional profile of the dried juice and pulp is 1 to 20 percent moisture, 0.1 to 15 percent protein, 0.1 to 20 percent fiber, and the vitamin and mineral content.

The filtered juice and the water from washing the wet pulp are preferably mixed together. The filtered juice may be vacuum evaporated to a brix of 40 to 70 and a moisture of 0.1 to 80 percent, more preferably from 25 to 75 percent. The resulting concentrated *Morinda citrifolia* juice may or may not be pasteurized. For example, the juice would not be pasteurized in circumstances where the sugar content or water activity was sufficiently low enough to prevent microbial growth. It is packaged for storage, transport and/or further processing.

The processed *Morinda citrifolia* product may also exist as a dietary fiber produced from the fruit puree. Still further, the processed *Morinda citrifolia* product may also exist in oil form, such as an oil extract. The *Morinda citrifolia* oil typically includes a mixture of several different fatty acids as triglycerides, such as palmitic, stearic, oleic, and linoleic fatty acids, and other fatty acids present in lesser quantities. In addition, the oil preferably includes an antioxidant to inhibit spoilage of the oil. Conventional food grade antioxidants are preferably used.

The *Morinda citrifolia* plant is rich in natural ingredients. Those ingredients that have been discovered include: (from the leaves): alanine, anthraquinones, arginine, ascorbic acid, aspartic acid, calcium, beta-carotene, cysteine, cystine, glycine, glutamic acid, glycosides, histidine, iron, leucine, isoleucine, methionine, niacin, phenylalanine, phosphorus, proline, resins, riboflavin, serine, beta-sitosterol, thiamine, threonine, tryptophan, tyrosine, ursolic acid, and valine; (from the flowers): acacetin-7-o-beta-d(+)-glucopyranoside, 5,7-dimethyl-apigenin-4'-o-beta-d(+)-galactopyranoside, and 6,8-dimethoxy-3-methylanthraquinone-1-o-beta-rhamnosyl-glucopyranoside; (from the fruit): acetic acid, asperuloside, butanoic acid, benzoic acid, benzyl alcohol, 1-butanol, caprylic acid, decanoic acid, (E)-6-dodeceno-gamma-lactone, (Z,Z,Z)-8,11,14-eicosatrienoic acid, elaidic acid, ethyl decanoate, ethyl hexanoate, ethyl octanoate, ethyl palmitate, (Z)-6-(ethylthiomethyl) benzene, eugenol, glucose, heptanoic acid, 2-heptanone, hexanal, hexanamide, hexanedioic acid, hexanoic acid (hexoic acid), 1-hexanol, 3-hydroxy-2-butanone, lauric acid, limonene, linoleic acid, 2-methylbutanoic acid, 3-methyl-2-buten-1-ol, 3-methyl-3-buten-1-ol, methyl decanoate, methyl elaidate, methyl hexanoate, methyl 3-methylthio-propanoate, methyl octanoate, methyl oleate, methyl palmitate, 2-methylpropanoic acid, 3-methylthiopropanoic acid, myristic acid, nonanoic acid, octanoic acid (octoic acid), oleic acid, palmitic acid, potassium, scopoletin, undecanoic acid, (Z,Z)-2,5-undecadien-1-ol, and vomifol; (from the roots): anthraquinones, asperuloside (rubichloric acid), damnacanthal, glycosides, morindadiol, morindine, morindone, mucilaginous matter, nor-damnacanthal, rubiadin, rubiadin monomethyl ether, resins, soranjidiol, sterols, and trihydroxymethyl anthraquinone-monomethyl ether; (from the root bark): alizarin, chlororubin, glycosides (pentose, hexose), morindadiol, morindanigrine, morindine, morindone, resinous matter, rubiadin monomethyl ether, and soranjidiol; (from the wood): anthragallol-2,3-dimethylether; (from the tissue culture): damnacanthal, lucidin, lucidin-3-primeveroside, and morindone-6beta-primeveroside; (from the plant): alizarin, alizarin-alpha-methyl ether, anthraquinones, asperuloside, hexanoic acid, morindadiol, morindone, morindogenin, octanoic acid, and ursolic acid.

Recently, as mentioned, many health benefits have been discovered stemming from the use of products containing *Morinda citrifolia*. One benefit of *Morinda citrifolia* is found in its ability to isolate and produce Xeronine, which is a relatively small alkaloid physiologically active within the body. Xeronine occurs in practically all healthy cells of plants, animals and microorganisms. Even though *Morinda citrifolia* has a negligible amount of free Xeronine, it contains appreciable amounts of the precursor of Xeronine, called Proxeronine. Further, *Morinda citrifolia* contains the inactive form of the enzyme Proxeronase which releases Xeronine from Proxeronine. A paper entitled, "The Pharmacologically Active Ingredient of Noni" by R. M. Heinicke of the University of Hawaii, indicates that *Morinda citrifolia* is "the best raw material to use for the isolation of xeronine," because of the building blocks of Proxeronine and Proxeronase. These building blocks aid in the isolation and production of Xeronine within the body. The function of the essential nutrient Xeronine is fourfold.

First, Xeronine serves to activate dormant enzymes found in the small intestines. These enzymes are critical to efficient digestion, calm nerves, and overall physical and emotional energy.

Second, Xeronine protects and keeps the shape and suppleness of protein molecules so that they may be able to pass through the cell walls and be used to form healthy tissue. Without these nutrients going into the cell, the cell cannot perform its job efficiently. Without Proxeronine to produce Xeronine our cells, and subsequently the body, suffer.

Third, Xeronine assists in enlarging the membrane pores of the cells. This enlargement allows for larger chains of peptides (amino acids or proteins) to be admitted into the cell. If these chains are not used they become waste.

Fourth, Xeronine, which is made from Proxeronine, assists in enlarging the pores to allow better absorption of nutrients.

Each tissue has cells which contain proteins which have receptor sites for the absorption of Xeronine. Certain of these proteins are the inert forms of enzymes which require absorbed Xeronine to become active. Thus Xeronine, by converting the body's procollagenase system into a specific protease, quickly and safely removes the dead tissue from skin. Other proteins become potential receptor sites for hormones after they react with Xeronine. Thus the action of *Morinda citrifolia* in making a person feel well is probably caused by Xeronine converting certain brain receptor proteins into active sites for the absorption of the endorphin, the well being hormones. Other proteins form pores through membranes in the intestines, the blood vessels and other body organs. Absorbing Xeronine on these proteins changes the shape of the pores and thus affects the passage of molecules through the membranes.

Because of its many benefits, *Morinda citrifolia* has been known to provide a number of anecdotal effects in individuals having cancer, arthritis, headaches, indigestion, malignancies, broken bones, high blood pressure, diabetes, pain, infection, asthma, toothaches, blemishes, immune system failure, and others.

The naturaceutical formulations or compositions containing one or more processed *Morinda citrifolia* products may be embodied in a form suitable for oral use, for example, as tablets, or lozenges, aqueous or oily suspensions, dispersible powders or granules, emulsions, syrups or elixirs. Compositions intended for oral use may be prepared according to any method known in the art for the manufacture of *Morinda citrifolia* compositions and such compositions may contain one or more agents selected from the group consisting of sweetening agents, flavoring agents, coloring agents and preserving agents. Tablets contain *Morinda citrifolia* in admixture with non-toxic pharmaceutically acceptable excipients which are suitable for the manufacture of tablets. These excipients may be for example, inert diluents, granulating and disintegrating agents, binding agents, and lubricating agents. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Aqueous suspensions contain the *Morinda citrifolia* in admixture with excipients suitable for the manufacture of aqueous suspensions. Such excipients are suspending agents, for example, sodium carboxymethyl-cellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitor monooleate, or condensation products of ethylene oxide with partial esters derived from fatty acids and hexitol anhydrides, for example polyethylene sorbitan monooleate.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The present invention naturaceutical formulation comprising one or more processed *Morinda citrifolia* products may also be embodied in a naturaceutical composition suitable for topical dermal application or administration, for example, as a lotion, gel, ointment, cream, oral medication, suppository, or others as commonly known in the art. The particular compositions comprising processed *Morinda citrifolia* intended for topical dermal application may be prepared according to any method known in the art for the manufacture of such topical dermal compositions and may comprise any known additional ingredients commonly used to produce topical dermal products. Moreover, the processed *Morinda citrifolia* products may be combined with various other ingredients commonly used to treat and prevent Candidiasis and similar related infections.

Present Invention Naturaceutical Formulations and Methods of Application

The present invention features a unique naturaceutical formulation and method of administering the same to inhibit the overgrowth of various microorganisms, such as *Bacillus cereus, Bacillus mycoids, Sarcina lutea, Candida albicans, Saccharomyces cerevisiae, Fusarium oxysporum* var. *vasinfectum, Macrophomina phaseoli, Diplodia oryzae, Rhizoctonia solani, Helminthosporium turcicum, Aspergillus carneus,* and others, and to induce antimicrobial activity, within the body of a mammal. Specifically, the present invention features a naturaceutical formulation adapted to inhibit overgrowth of *candida albicans* and to treat or combat and prevent Candidiasis. The present invention functions to advance prior art treatments of Candidiasis by providing a naturaceutical composition formulated with one or more processed *Morinda citrifolia* products as derived from the Indian Mulberry plant. The *Morinda citrifolia* product is incorporated into various carriers suitable for in vivo treatment of a patient. For instance, the naturaceutical formulation may be ingested orally via an oral composition, applied topically via a topical dermal composition, introduced through an intravenous injection or feeding, or otherwise internalized as is appropriate and directed.

Overgrowth of microorganisms, such as *candida albicans*, lead to several known diseases or infections, collectively known as Candidiasis. As stated, microorganisms *Candida albicans*, and other strains of *Candida*, are yeast or yeast-like fungi that are capable of growing on and within the human body and that normally or naturally inhabit our digestive system: the mouth, throat, intestines and genitourinary tract. *Candida* is a normal part of the bowel flora (the organisms that naturally live inside our intestines, and are not parasitic). It has many functions inside our digestive tract, one of them which is to recognize and destroy harmful bacteria. Without *Candida albicans* in our intestines we would be defenseless against many pathogenic bacteria. Under normal circumstances, a healthy individual can have millions of *Candida albicans* in their system.

Our immune system is supposed to keep these organisms under control, together with various strains of friendly bacteria, such as *Lactobacillus acidophilus, B. bifidum, Lactobacillus bulgaricus, S. thermophilus,* and *L. salivarius*. However, if the number of friendly bacteria is decreased (e.g., as a result of antibiotics, pesticides, chlorine, etc.) in relation to the number of *Candida,* the immune system is weakened and other conditions for yeast proliferation occur (e.g., improper pH in the digestive system, or high sugar diet). *Candida albicans* will shift from yeast to a mycelial fungal form and start to invade the body. In the yeast state *Candida albicans* are a non-invasive, sugar-fermenting organism, while in the fungal state they are invasive and can produce rhizoids, which are very long root-like structures. Rhizoids can penetrate mucosa or intestinal walls, leaving microscopic holes and allowing toxins, undigested food particles and bacteria and yeast to enter the bloodstream.

The naturaceutical composition of the present invention comprises one or more processed *Morinda citrifolia* products present in an amount by weight between about 0.01 and 100 percent by weight, and preferably between 0.01 and 95 percent by weight. Several embodiments of formulations are provided below. However, these are only intended to be exemplary as one ordinarily skilled in the art will recognize other formulations or compositions comprising one or more processed *Morinda citrifolia* products.

The processed *Morinda citrifolia* product present as an ingredient in a given or identified amount in the naturaceutical formulation is intended to function as the active ingredient or contain one or more active ingredients, such as Quercetin and Rutin, and others, for effectuating the inhibition and prevention of the overgrowth of *candida albicans*, in relation to the several "friendly" bacteria, within a mammal often resulting in Candidiasis, as well as for treating or relieving pre-existing infections of Candidiasis, by inhibiting or preventing further growth of *candida albicans* and inducing antimicrobial activity within the body.

Active ingredients may be extracted out using various alcohol or alcohol-based solutions, such as methanol, ethanol, and ethyl acetate, and other alcohol-based derivatives using any known process in the art. In an exemplary embodiment, the active ingredients of Quercetin and Rutin are present in amounts by weight ranging from 0.01-10 percent of the total formulation or composition. However, these amounts may be concentrated into a more potent concentration, in which they are present in amounts ranging from 10 to 100 percent of the total composition.

The processed *Morinda citrifolia* product may be formulated with various other additional ingredients to produce several different intended purpose or use compositions and types of compositions, such as an oral naturaceutical composition, a topical dermal naturaceutical composition, a systemically administered naturaceutical composition, or others. The additional ingredients to be utilized in any of the above-mentioned naturaceutical compositions are any that are safe for introduction into the body of a mammal, and particularly a human, and may exist in various forms, such as liquids, tablets, lozenges, aqueous or oily solutions, dispersible powders or granules, emulsions, syrups, elixirs, lotions, creams, gels, suppositories, ointments, etc.

In one exemplary embodiment, the present invention features a method of administering a naturaceutical composition to a mammal for the treatment of Candidiasis and its related conditions. The method comprises the steps of (a) formulating a naturaceutical composition comprising in part a processed *Morinda citrifolia* product present in an amount between about 0.01 and 100 percent by weight, and preferably 0.1 to 95 percent by weight, wherein the composition also comprises a carrier, such as water or purified water, and other natural or artificial ingredients; (b) administering the naturaceutical composition into the body such that the *Morinda citrifolia* is sufficiently internalized and concentrated within the infected area, thus capable of inducing antimicrobial activity therein, and to inhibit and prevent further growth of *candida albicans;* (c) repeating the above steps as often as necessary to provide an effective amount of *Morinda citrifolia* to the area or region infected with Candidiasis.

In one exemplary embodiment, the step of administering the naturaceutical composition into the body comprises ingesting the composition orally through one of several means. Specifically, the naturaceutical composition may be formulated as a liquid, gel, solid, or some other type that would allow the composition to be quickly digested and concentrated within the infected area. It is important to note that the step of administering the naturaceutical composition should be carried out in an effective manner so that the greatest concentration of naturaceutical composition is allowed to be internalized. For the naturaceutical composition to take effect, it must be sufficiently internalized into the body where it may then begin to act upon the overgrowth of *candida albicans* within the body. Moreover, since the naturaceutical composition will most likely be consumed orally, it may contain one or more agents selected from the group consisting of sweetening agents, flavoring agents, coloring agents, preserving agents, and other medicinal agents as directed.

In another exemplary embodiment, the step of administering the naturaceutical composition into the body comprises applying a topical dermal composition, comprising processed *Morinda citrifolia* as at least one existing ingredient in the composition, to the area affected or infected with Candidiasis. The ingredients to be utilized in a topical dermal composition are also any that are safe for internalizing into the body of a mammal and may exist in various forms, each comprising one or more carrier agents. The topical dermal naturaceutical composition is applied directly to the infected area as often as needed until growth, or overgrowth, is abated.

In still another exemplary embodiment, the step of administering the naturaceutical composition into the body comprises systemically introducing the processed *Morinda citrifolia* product-based naturaceutical composition into the body via any known means in the art, such as intravenously. The ingredients for the systemically administered formulation may also comprise any commonly known in the art.

In still another exemplary embodiment, the step of administering the naturaceutical composition may include injecting the composition into the body using an intravenous pump. This technique is advantageous as it would allow the composition to be localized in the area where it would have the most effect, or the area that would provide for the greatest concentration of the naturaceutical composition.

The treatment of Candidiasis by inhibiting the overgrowth of *candida albicans,* or inducing antimicrobial activity within the body, results from the affect of these processed *Morinda citrifolia* products, and/or the active ingredients found therein, namely Quercetin, Rutin, Xeronine, and the building blocks to Xeronine—Proxeronase and Proxeronine, on the life of these organisms and their ability to survive. Specifically, the processed *Morinda citrifolia* products, whether they be in the form of fruit juice, puree juice, dietary fiber, oil, etc., function to inhibit and prevent growth by providing an ingredient or substance that is lethal, or at least significantly inhibitory, to *Candida,* thus restoring a more natural balance between *candida albicans* (fungus) and friendly bacteria.

In another exemplary embodiment, the naturaceutical composition is internalized by orally ingesting between 1 teaspoon and 2 oz., and preferably 2 oz., every two hours each day, or at least twice a day until the growth or overgrowth is abated. This process should be maintained even after the growth is abated to prevent further overgrowth or latent overgrowth. Also, the naturaceutical composition should be taken on an empty stomach, which means a period of time at least two hours prior to consumption of any food or drink. Following this, the naturaceutical composition actively impairs growth of the *Candida* and even functions to kill many of these organisms, thereby combating the effects of Candidiasis. Of course, one ordinarily skilled in the art will recognize that the amount of composition and frequency of use may vary from individual to individual.

The following tables illustrate or represent some of the preferred formulations or compositions contemplated by the present invention. As stated, these are only intended as exemplary embodiments and are not to be construed as limiting in any way.

Formulation One

| Ingredients | Percent by Weight |
| --- | --- |
| *Morinda citrifolia* puree juice or fruit juice | 100% |

Formulation Two

| Ingredients | Percent by Weight |
| --- | --- |
| *Morinda citrifolia* fruit juice | 10-99.99% |
| water | 0.1-90% |

Formulation Three

| Ingredients | Percent by Weight |
| --- | --- |
| *Morinda citrifolia* fruit juice | 10-99.99% |
| non-*Morinda citrifolia*-based fruit juices | 0.1-90% |

Formulation Four

| Ingredients | Percent by Weight |
| --- | --- |
| *Morinda citrifolia* fruit juice | 50-90% |
| water | 0.1-50% |
| non-*Morinda citrifolia*-based fruit juices | 0.1-30% |

Formulation Five

| Ingredients | Percent by Weight |
| --- | --- |
| *Morinda citrifolia* puree juice | 10-99.9% |
| water | 0.1-90% |

Formulation Six

| Ingredients | Percent by Weight |
| --- | --- |
| *Morinda citrifolia* puree juice | 10-99.9% |
| non-*Morinda citrifolia*-based fruit juices | 0.1-90% |

Formulation Seven

| Ingredients | Percent by Weight |
|---|---|
| *Morinda citrifolia* puree juice | 50-90% |
| water | 0.1-50% |
| non-*Morinda citrifolia*-based fruit juices | 0.1-30% |

Formulation Eight

| Ingredients | Percent by Weight |
|---|---|
| *Morinda citrifolia* dietary fiber | 0.1-30% |
| water | 1-99.9% |
| non-*Morinda citrifolia*-based fruit juices | 1-99.9% |

Formulation Nine

| Ingredients | Percent by Weight |
|---|---|
| *Morinda citrifolia* dietary fiber | 0.1-30% |
| water | 1-99.9% |
| *Morinda citrifolia* fruit juice or puree juice | 1-99.9% |

Formulation Ten

| Ingredients | Percent by Weight |
|---|---|
| *Morinda citrifolia* oil | 0.1-30% |
| carrier medium | 70-99.9% |
| other ingredients | 1-95% |

Formulation Eleven

| Ingredients | Percent by Weight |
|---|---|
| *Morinda citrifolia* fruit or puree juice/concentrate, oil, or dietary fiber | 10-80% |
| carrier medium | 20-90% |

Formulation Twelve

| Ingredients | Percent by Weight |
|---|---|
| *Morinda citrifolia* fruit or puree juice/concentrate, oil, or dietary fiber | 5-80% |
| carrier medium | 20-95% |

Formulation Thirteen

| Ingredients | Percent by Weight |
|---|---|
| *Morinda citrifolia* oil or oil extract | 0.1-20% |
| carrier medium | 20-90% |

Formulation Fourteen

| Ingredients | Percent by Weight |
|---|---|
| *Morinda citrifolia* puree juice or fruit Juice | 0.1-80% |
| *Morinda citrifolia* oil | 0.1-20% |
| carrier medium | 20-90% |

Formulation Fifteen

| Ingredients | Percent by Weight |
|---|---|
| *Morinda citrifolia* puree juice concentrate or fruit juice concentrate | 100% |

Formulation Sixteen

| Ingredients | Percent by Weight |
|---|---|
| *Morinda citrifolia* fruit juice concentrate or puree juice concentrate | 85-99.99% |
| water | 0.1-15% |

Formulation Seventeen

| Ingredients | Percent by Weight |
|---|---|
| *Morinda citrifolia* fruit juice | 10-80% |
| topical carrier composition | 20-90% |

Formulation Eighteen

| Ingredients | Percent by Weight |
|---|---|
| *Morinda citrifolia* oil | 0.1-80% |
| topical carrier composition | 20-99.9% |

Formulation Nineteen

| Ingredients | Percent by Weight |
|---|---|
| *Morinda citrifolia* oil | 0.1-20% |
| *Morinda citrifolia* fruit juice | 0.1-80% |
| topical carrier composition | 20-90% |

Formulation Twenty

| Ingredients | Percent by Weight |
|---|---|
| *Morinda citrifolia* oil | 0.1-20% |
| *Morinda citrifolia* fruit juice | 0.1-80% |
| isopropyl myristate | 10-20% |
| purified water | 20-30% |
| glycerin | 1-20% |
| octyl cocoate | 1-20% |
| hydrogenated coco-glycerides | 1-20% |
| Stearyl alcohol | 1-5% |
| cetyl alcohol | 1-5% |
| butylene glycol | 1-5% |
| caprylic/capric triglyceride | 1-5% |
| glyceryl stearate citrate | 1-5% |
| shea butter | 1-5% |
| tocopheryl acetate (Vitamin E) | 1-5% |
| biosaccharide gum | 1-5% |
| macadamia nut oil | 1-5% |
| ubiquinone (coenzyme Q10) | 1-5% |
| retinyl palmitate (Vitamin A) | 1-5% |
| sodium ascorbyl phosphate (Vitamin C) | 1-5% |
| tridecyl ttearate | 1-5% |
| tridecyl trimellitate | 1-5% |
| dipentaerylthirtyl hexacaprylatel hexacaprate | 1-5% |
| lanolin alcohol | 1-5% |
| carbomer | 1-5% |
| sodium hydroxide | 1-5% |
| trisodium EDTA | 1-5% |
| phenoxyethanol | 1-5% |
| methylparaben | 1-5% |
| ehylparaben | 1-5% |
| propylparaben | 1-5% |
| butylparaben | 1-5% |
| dMDM Hydantoin | 1-5% |

In another exemplary embodiment, a person suffering from Candidiasis as described above takes, or is administered, orally at least one (1) ounce of the naturaceutical composition identified in Formulation One in the morning on an empty stomach, and at least one (1) ounce at night on an empty stomach, just prior to retiring to bed. This procedure is carried out using this dosage until the growth is abated. The procedure may be continued however, to effectuate prevention of future infections of Candidiasis and to prevent the overgrowth of *candida albicans*. In one example, which is not meant to be limiting in any way, the beneficial *Morinda Citrifolia* fruit juice product is processed into Tahitian Noni® juice (TNJ) manufactured by *Morinda,* Incorporated of Orem, Utah. A similar procedure may be carried out using the naturaceutical compositions identified in Formulations Two through Formulation Nine.

As stated above, another exemplary embodiment of the present invention features a method for introducing a topical dermal naturaceutical composition or formulation to a region of the body infected by Candidiasis. This method essentially comprises the application of a naturaceutical composition, embodied in a topical dermal composition, to the skin or mucosa of the patient, wherein the naturaceutical is absorbed or internalized into the body through the pores or membrane. Several embodiments of the topical dermal naturaceutical comprising various different ingredients are contemplated for use herein, with each embodiment comprising one or more forms of a processed *Morinda citrifolia* product as the active ingredient as taught and explained herein, along with one or more carrier agents or mediums and any other ingredients commonly known in the art that are appropriate for a topical dermal composition.

In one exemplary embodiment, the topical dermal naturaceutical comprises the ingredients of: a processed *Morinda citrifolia* product present in an amount by weight between about 10-80 percent; and a carrier medium or composition present in an amount by weight between about 20-90 percent.

In this embodiment, the processed *Morinda citrifolia* product may comprise one or more of processed *Morinda citrifolia* fruit juice (in dilute or concentrate form), processed *Morinda citrifolia* puree juice (in dilute or concentrate form), processed *Morinda citrifolia* dietary fiber, and/or processed *Morinda citrifolia* oil or oil extract. Moreover, this composition may comprise extracted *Morinda citrifolia* products, such as *Morinda citrifolia* ethyl extracts, *Morinda citrifolia* ethanol extracts, *Morinda citrifolia* methanol extracts, etc.

In another exemplary embodiment, the topical dermal naturaceutical comprises the ingredients of: processed *Morinda citrifolia* fruit juice or puree juice (in dilute or concentrate form) present in an amount by weight between about 0.1-80 percent; processed *Morinda citrifolia* oil present in an amount by weight between about 0.1-20 percent; and a carrier medium or composition present in an amount by weight between about 20-90 percent. The topical dermal composition may also be formulated with a *Morinda citrifolia* dietary fiber product in similar concentrations.

Formulations Ten through Fourteen and Formulations Eighteen through Twenty, each identified above, are examples of some of the ingredients and their concentrations that may be incorporated into the topical dermal naturaceutical.

The carrier medium or composition in the topical dermal naturaceutical may comprise any ingredient capable of being safely introduced into the body of a mammal, and that is also capable of providing the carrying medium for the processed *Morinda citrifolia* product. Specific carrier mediums and compositions are well known in the art and not described in detail herein. however, Formulation Twenty identified above illustrates one exemplary embodiment of some of the types of ingredients that may be incorporated into the naturaceutical. Overall, the purpose of the carrier medium is as stated, to provide a means to embody the processed *Morinda citrifolia* product within the topical dermal naturaceutical for the purpose of providing the ability to introduce the naturaceutical into the body, and particularly, into an area or region infected with Candidiasis.

The present invention further features taking a prescribed or over the counter pharmaceutical medication or drug, formulated for the treatment and prevention of Candidiasis, concurrently with one of the *Morinda citrifolia*-based naturaceutical formulations described herein. Taking or administering the *Morinda citrifolia*-naturaceutical formulation concurrently with a Candidiasis medication functions to enhance the relief potential for the patient by increasing or enhancing the efficacy of the Candidiasis medication, as well as providing the same benefits and advantages to the patient that are obtained directly from the *Morinda citrifolia*-naturaceutical formulation. Pharmaceuticals used to treat and prevent Candidiasis are well known in the art and can be grouped into two different categories—symptomatic relief and preventive therapy. Symptomatic relief medications are used to relieve symptoms associated with existing Candidiasis, while preventive medications are used to reduce some of the factors that contribute to the onset of a Candidiasis infection, or rather prevent the overgrowth of *Candida*.

The processed *Morinda citrifolia* products comprise the active ingredients Quercetin and Rutin. These active ingredients are is effective against *Candida albicans* because of their ability to The following examples set forth and present the effects of *Morinda citrifolia* on healthy and degenerating cartilage, as well as the preventative and treatment effects of *Morinda citrifolia* against Candidiasis. These examples are not intended to be limiting in any way, but are merely illustrative of the benefits and advantageous, as well as the remedial effects, of *Morinda citrifolia* on Candidiasis.

EXAMPLE ONE

In this example, a female patient has a vaginal yeast infection caused by the *Candida albicans* fungus. The individual suffering from the infection has itching, burning, redness, and irritation in the vaginal area. The individual desires to treat the condition with a nonprescription, over-the-counter preparation. To treat the infection, the individual consumes a prescribed amount of a naturaceutical food product composition containing processed *Morinda citrifolia* fruit or puree juice. The person intermittently consumes the food product containing the processed *Morinda citrifolia* juice until the symptoms of the infection are relieved and/or the infection is reduced or eliminated. Alternatively, the person applies a topical dermal naturaceutical comprising a processed *Morinda citrifolia* product to the infected area at least twice a day until growth is abated and the yeast infection is eliminated.

EXAMPLE TWO

In this example, a person is suffering from a disorder that increases the likelihood that the person will contract Candidiasis. For example, the person may have a thyroid disorder, an endocrine disorder, or be suffering from diabetes. The person consumes a naturaceutical food product composition containing processed *Morinda citrifolia* fruit or puree juice in order to reduce the likelihood that the person will contract Candidiasis. In the event the person does contract Candidiasis, the consumption of the naturaceutical food product containing *Morinda citrifolia* juice helps to contain the infection and limit the ability for the infection to spread to other areas or regions.

EXAMPLE THREE

In this example, an individual is taking medications or receiving medical treatments for an ailment other than Candidiasis. Receiving the treatment or taking the medication increases the likelihood that the person could contract Candidiasis. For example, the person may be taking hormonal treatments, corticosteroids, or high estrogen contraceptives. The person may be undergoing cancer or HIV therapy, or may be using antibiotics. Additionally, the person may be concerned that taking medications to limit or prevent yeast infection could adversely react or reduce the effectiveness of the medication the person is already taking. The person consumes a naturaceutical food product containing processed *Morinda citrifolia* puree juice during the period of time that the medication is being taken in order to prevent a yeast infection and offset the increased likelihood of infection. The individual may begin taking the food product containing processed *Morinda citrifolia* puree juice for a period of time prior to taking the medication in order to further decrease the chance of yeast infection.

EXAMPLE FOUR

In this example, a woman is pregnant rendering her more susceptible to yeast infection. The pregnant woman is unable to take medications to treat a yeast infection because there is the potential for the yeast infection medication to pass through the placenta to the embryo or fetus. In order to reduce the likelihood of a yeast infection or to treat an existing yeast infection, the pregnant woman consumes a naturaceutical composition comprising processed *Morinda citrifolia* puree or fruit juice. Pharmaceutically beneficial active ingredients in the *Morinda citrifolia* juice prevent or substantially reduce the woman's chance of contracting yeast infection and help to combat any existing yeast infections.

EXAMPLE FIVE

In this example, a person is suffering a condition having associated symptoms similar to those experienced by a person suffering from Candidiasis. The person suffering from the condition is uncertain as to whether or not he or she is suffering from Candidiasis. Rather than attempting to self-prescribe Candidiasis medication such as over-the-counter ointments or creams, the person consumes a naturaceutical food product comprising processed *Morinda citrifolia* puree or fruit juice in order to alleviate the symptoms from which the person suffers.

EXAMPLE SIX

In an actual example as reported by Dr. Scott Gerson, preliminary evaluations of the anti-fungal activity of extracts of *Morinda citrifolia* were found to be positive. In his study an mean inhibitory concentration (MIC) protocol was developed and then used to test ethanol, methanol, ethyl acetate, and aqueous extracts of *Morinda citrifolia* dried and then diluted to a final concentration of 2 mg/ml for anti-microbial activity against *A. niger* (ATCC 6275), *C. albicans* (ATCC 10231), *E. coli* (ATCC 25922), *S. aureus* (ATCC 25923), and *T. mentagrophytes* (ATCC 9533). These extracts each contained the isolated and extracted active ingredients of Quercetin, Rutin, and others as derived or obtained from the *Morinda citrifolia*. Liquid extracts were obtained and tested in micro titer wells in duplicate. Quantities of the extracts, ranging from 6 micro liters to 200 micro liters, were placed in the wells and dried. A McFarland 0.5 solution of each organism was prepared, and a 1/100 suspension into the appropriate media was made. This organism suspension was added to each well, and incubated for an appropriate amount of time at the appropriate temperature. Plates were then examined for growth, and MIC's were determined. All duplicate results agreed within one dilution.

The ethyl acetate extracts had the least amount of anti-microbial activity, only showing activity when tested against *T. mentagrophytes* and *S. aureus*. The ethanol extracts showed anti-microbial activity against all of the organisms tested. This activity ranged from off-scale on the low end when tested against *T. mentagrophytes*, to high on-scale results for *A. niger*. Methanol extracts also showed significant activity against all of the organisms tested, and ranged from off-scale on the low end when tested against *T. mentagrophytes*, to high on-scale results for *A. niger*. These results indicate that extracts of *Morinda citrifolia* contain anti-microbial activity most significantly against various strains of fungi.

EXAMPLE SEVEN

The following example details another actual study conducted and the results achieved. The purpose of the study was to determine mean inhibitory concentration (MIC) and mean lethal concentration (MLC) of selected *Morinda citrifolia* extracts as processed and produced according to the disclosure herein against three common pathogenic fungi and two common bacteria, and particularly to determine the effectiveness of using *Morinda citrifolia* to treat Candidiasis.

The fungus and bacteria organisms or species used in the test were *Candida albicans* (ATCC #10231), *E. coli* (0157H7 ATCC #43888), *S. aureus* (ATCC #6538), *B. subtilis* (ATCC #19659), *S. choleraesuis serotype enteritidis* (ATCC #13706), and *L. monocytogenes* (ATCC #19111).

The procedure used was a standard assay for antimicrobials, which incorporate the procedures, intent and content of the American Society for Microbiology recommended methodology. The antimicrobial agents were Tahitian Noni® Puree Juice (TNPJ) in different concentration(s).

The method outlined below is a summary of the methods used in the Minimum Inhibitory Concentration (MIC) and Minimum Lethal Concentration (MLC) procedures. First, the organisms were obtained from ATCC. Second, upon arrival, the organisms were transferred from stock to Casein Digest Broth (SCDB). Third, bacterial cultures were incubated at 35-39 degrees Celsius for 18-24 hours while the yeast was cultured at 20-25 degrees Celsius for 2-5 days.

MIC Test Procedure

The following outlines the test procedure for the mean inhibitory concentration:
1. The TNPJ concentrate, in triplicate, was diluted serially 1:2 in sterile water out to 1:32. The dilutions were added to an equal volume if 2× SCBD to provide an additional 1:2 dilution making the final dilutions tested in the range of 1:2 to 1:64 for all organisms except *B. subtilis*. *B. subtilis* was tested at final dilutions ranging from 1:2 to 1:8.
2. Three negative control tubes were prepared by mixing the highest dilution tested of the TNPJ with equal volumes of 2× SCBD and NO tested organisms were added. Also, three tubes were used as positive control tubes for EACH organisms were prepared by mixing sterile water with equal volumes of 2× SCBD.
3. Concomitantly, 0.05 mL of suspension was added to corresponding test sample dilution and positive control tubes for each test organism. Bacterial and fungal species test tubes were incubated as previously described.
4. An aliquot from each tube was streaked onto appropriate agar to confirm the presence or growth after incubation. Bacterial aliquot were plated on SCBD and yeast on SDEX and incubated as previously described.
5. After confirmation of growth, the growth was scored as either negative (0) or positive (+) for each tube.

MLC Test Procedure

The following outlines the test procedure for the mean lethal concentration. This procedure will test only the tubes either suspected or confirmed of NOT having growth after MIC testing were tested for MLC.
1. Serial dilutions (1/10) were made to neutralize broth up to a dilution of 1/1000. An aliquot from each dilution was plated onto neutralizer agar (NUAG). As a negative control, 2× SCBD was plated onto NUAG and incubated in temperature and time/day as preciously described for bacterial and fungi.
2. The neutralization was verified as follows. The lowest dilution of TNPJ tested for MLC was tested for neutralization recovery of the test organisms in 2× SCBD. In triplicate, 0.5 mL aliquots of the diluted test product were plated on NUAG. The plates were spiked with 10-100 CFU of the tested organisms. For comparison, three plates of NUAG without the test product were also spiked with the same 10-100 CFU of the test organism as a positive control for both neutralization and MLC.

Results Obtained for MIC Test

TABLE #1

| MIC results for *E. coli* | | | |
|---|---|---|---|
| Dilution | Growth (+/0) | | |
| 1:2 | 0 | 0 | 0 |
| 1:4 | + | + | + |
| 1:8 | + | + | + |
| 1:16 | + | + | + |
| 1:32 | + | + | + |
| 1:64 | + | + | + |
| Positive | + | + | + |
| Negative | 0 | 0 | 0 |
| Media | 0 | 0 | 0 |

Titer: $2.0 \times 10^8$ CFU/mL
Inoculating volume = 0.05 mL

TABLE #2

| MIC results for *S. aureus* | | | |
|---|---|---|---|
| Dilution | Growth (+/0) | | |
| 1:2 | 0 | 0 | 0 |
| 1:4 | + | + | + |
| 1:8 | + | + | + |
| 1:16 | + | + | + |
| 1:32 | + | + | + |
| 1:64 | + | + | + |
| Positive | + | + | + |
| Negative | 0 | 0 | 0 |
| Media | 0 | 0 | 0 |

Titer: $1.0 \times 10^8$ CFU/mL
Inoculating volume = 0.05 mL

TABLE #3

| MIC results for *B. subtilis* | | | |
|---|---|---|---|
| Dilution | Growth (+/0) | | |
| 1:2 | 0 | 0 | 0 |
| 1:4 | + | + | + |
| 1:8 | + | + | + |
| Positive | + | + | + |
| Negative | 0 | 0 | 0 |
| Media | 0 | 0 | 0 |

Titer: $1.4 \times 10^8$ CFU/mL
Inoculating volume = 0.05 mL

TABLE #4

| MIC results for *Salmonella choleraesuis* serotype *enteritidis* | | | |
|---|---|---|---|
| Dilution | Growth (+/0) | | |
| 1:2 | 0 | 0 | 0 |
| 1:4 | + | + | + |
| 1:8 | + | + | + |
| 1:16 | + | + | + |
| 1:32 | + | + | + |
| 1:64 | + | + | + |
| Positive | + | + | + |
| Negative | 0 | 0 | 0 |
| Media | 0 | 0 | 0 |

Titer: $3.4 \times 10^8$ CFU/mL
Inoculating volume = 0.05 mL

TABLE #5

**MIC results for *Listeria monocytogenes***

| Dilution | Growth (+/0) | | |
|---|---|---|---|
| 1:2 | 0 | 0 | 0 |
| 1:4 | + | + | + |
| 1:8 | + | + | + |
| 1:16 | + | + | + |
| 1:32 | + | + | + |
| 1:64 | + | + | + |
| Positive | + | + | + |
| Negative | 0 | 0 | 0 |
| Media | 0 | 0 | 0 |

Titer: $1.1 \times 10^8$ CFU/mL
Inoculating volume = 0.05 mL

TABLE #6

**MIC results for *Candida albicans***

| Dilution | Growth (+/0) | | |
|---|---|---|---|
| 1:2 | 0 | 0 | 0 |
| 1:4 | + | + | + |
| 1:8 | + | + | + |
| 1:16 | + | + | + |
| 1:32 | + | + | + |
| 1:64 | + | + | + |
| Positive | + | + | + |
| Negative | 0 | 0 | 0 |
| Media | 0 | 0 | 0 |

Titer: $1.1 \times 10^8$ CFU/mL
Inoculating volume = 0.05 mL

Results Obtained for MLC Test

TABLE #7

*E. coli*

| Tube Replicate | Dilution (+/0) | | |
|---|---|---|---|
| | $10^{-1}$ | $10^{-2}$ | $10^{-3}$ |
| 1:2 #1 | 0 | 0 | 0 |
| 1:2 #2 | 0 | 0 | 0 |
| 1:2 #3 | 0 | 0 | 0 |

TABLE #8

*S. aureus*

| Tube Replicate | Dilution (+/0) | | |
|---|---|---|---|
| | $10^{-1}$ | $10^{-2}$ | $10^{-3}$ |
| 1:2 #1 | + | 0 | 0 |
| 1:2 #2 | + | 0 | 0 |
| 1:2 #3 | 0 | 0 | 0 |

TABLE #9

*B. subtilis*

| Tube Replicate | Dilution (+/0) | | |
|---|---|---|---|
| | $10^{-1}$ | $10^{-2}$ | $10^{-3}$ |
| 1:2 #1 | + | + | 0 |
| 1:2 #2 | + | + | 0 |
| 1:2 #3 | + | 0 | 0 |
| 1:4 #1 | + | 0 | 0 |
| 1:4 #2 | + | 0 | 0 |
| 1:4 #3 | + | 0 | 0 |
| 1:8 #1 | + | + | + |
| 1:8 #2 | + | + | + |
| 1:8 #3 | + | + | + |

TABLE #10

***Salmonella choleraesuis* serotype *enteritidis***

| Tube Replicate | Dilution (+/0) | | |
|---|---|---|---|
| | $10^{-1}$ | $10^{-2}$ | $10^{-3}$ |
| 1:2 #1 | 0 | 0 | 0 |
| 1:2 #2 | 0 | 0 | 0 |
| 1:2 #3 | 0 | 0 | 0 |

TABLE #11

*Listeria monocytogenes*

| Tube Replicate | Dilution (+/0) | | |
|---|---|---|---|
| | $10^{-1}$ | $10^{-2}$ | $10^{-3}$ |
| 1:2 #1 | 0 | 0 | 0 |
| 1:2 #2 | 0 | 0 | 0 |
| 1:2 #3 | + | 0 | 0 |

TABLE #12

*Candida albicans*

| Tube Replicate | Dilution (+/0) | | |
|---|---|---|---|
| | $10^{-1}$ | $10^{-2}$ | $10^{-3}$ |
| 1:2 #1 | 0 | 0 | 0 |
| 1:2 #2 | 0 | 0 | 0 |
| 1:2 #3 | 0 | 0 | 0 |

TABLE 13

Neutralization

| Organism | Positive Count | | | | Neutralization Count | | | | Percent Recovery |
|---|---|---|---|---|---|---|---|---|---|
| | 1 | 2 | 3 | Ave | 1 | 2 | 3 | Ave | |
| E. coli | 15 | 14 | 16 | 15 | 23 | 17 | 18 | 19 | 127% |
| S. aureus | 56 | 54 | 61 | 57 | 82 | 60 | 71 | 71 | 125% |
| B. subtilis | 86 | 91 | 88 | 88 | 70 | 62 | 61 | 64 | 73% |
| S. choleraesuis | 34 | 11 | 26 | 24 | 35 | 28 | 17 | 27 | 113% |
| L. monocytogenes | 79 | 72 | 81 | 77 | 73 | 69 | 74 | 72 | 94% |
| Candida albicans | 54 | 53 | 49 | 52 | 45 | 52 | 72 | 56 | 108% |

Results Summary

The MIC test results revealed that *B. subtilis* was the only organism that survived all dilutions of the test product while the others were NOT recoverable as confirmed by the streak plates' results for the 1:2 dilution, as shown in Tables 1-6. In other words, the test product was lethal and inhibitory at the indicated dilution.

The result of the MLC test confirmed that the product was also lethal to *E. coli, S. choleraesuis serotype enteritidis* and *Candida albicans*.

However, the test product was inhibitory to the *S. aureus* and *L. monocytogenes* while it has no effect on the growth of *B. subtilis*. That is to say, that none of the dilutions indicated have an effect on the growth of *B. subtilis*.

EXAMPLE EIGHT

Similar to the other above-identified examples, the purpose of this experiment was to determine mean inhibitory concentration (MIC) of selected processed *Morinda citrifolia* fruit juice extracts against three common pathogenic fungi and two common bacteria, namely, *Aspergillus niger* (ATCC 6275), *Candida albicans* (ATCC 10231), *Trichophyton mentagrophytes* (ATCC 9533), *Staphlococcus aureus* (ATCC 29213), and *Escherichia coli* (ATCC 9533).

The processed *Morinda citrifolia* extracts comprised ethanol, methanol, ethyl acetate, and aqueous extracts. Each of these was prepared using appropriate solvents.

Sterile Media Preparations (1 Liter)
1. Fungi: Sabouraud Dextrose Broth
2. Bacteria: Mueller Hinton Broth
3. Autoclave at 121° C. for 20 minutes Organism Suspension Preparations
1. Plated each organism on appropriate media.
2. Incubated and confirmed identity.
3. Prepared 0.5 McFarland suspension of each organism.
4. Added 0.1 ml of the organism to 9.9 ml of the appropriate media (SDB or MHB).

Preparation of *Morinda citrifolia* Extracts

Using appropriate media, the extracts were dried and then diluted to a final concentration of 2 mg/ml. These 2 mg/ml final volumes were used as *Morinda citrifolia* stock solutions. The extracts were stored in −20° C. freezers until ready for fungal plating.

Thirteen test tubes were labeled as follows: 1/1, 1/32, 1/512, 1/2, 1/64, 1/1024, 1/4, 1/128 GC (Growth Control), 1/8, 1/256, NC (Non-inoculated Control), and 1/16. The following procedures were then performed:

1. 100 µl of *Morinda citrifolia* stock solution was added to Tube 1/1 and 100 µl to Tube 1/2.
2. 100 µl of *sterile media* was added to Tubes: 1/2, 1/4, 1/8, 1/16, 1/32, 1/62, 1/128, 1/256, 1/512, 1/1024, GC, and NC.
3. Tube 1/2 was mixed well and 100 l removed and added to Tube 1/4.
4. The two-fold dilution procedure was continued for Tubes 1/8, 1/16, 1/32, 1/64, 1/128, 1/256, 1/512, and 1/1024.
5. Discarded 100 l from Tube 1/1024. No diluted TNJ solution was added to Tubes GC or NC. These were the control tubes.
6. At this point all tubes contained 100 l.
7. Because it was known that 2 mg/ml (i.e. 2000 g/ml) of the extract stock solution was initially started with, the serial two-fold dilution resulted in the following concentrations of TNJ extract:

| Concentration of TNJ Extract in Each Tube | | |
|---|---|---|
| Tube Number | Dilution | Concentration of Extract |
| 1 | 1/1 | 2000 ug/ml |
| 2 | 1/2 | 1000 ug/ml |
| 3 | 1/4 | 500 ug/ml |
| 4 | 1/8 | 250 ug/ml |
| 5 | 1/16 | 125 ug/ml |
| 6 | 1/32 | 62.50 ug/ml |
| 7 | 1/64 | 31.25 ug/ml |
| 8 | 1/128 | 15.13 ug/ml |
| 9 | 1/256 | 7.56 ug/ml |
| 10 | 1/512 | 3.78 ug/ml |
| 11 | 1/1024 | 1.89 ug/ml |
| 12 | GC | No extract |
| 13 | NC | No organism |

Inoculation

The inoculation procedure was performed as follows:
1. 100 ul of organism suspension was added to all of the tubes except Tube NC (non-inoculated control).
2. 100 ul of additional media was added to NC.
3. All tubes were incubated at the appropriate temperatures and intervals:

Fungi: 25° C. for 5-7 days
Bacteria: 37° C. for 24-48 hours

Recording Results by Observing Turbidity

Turbidity was closely examined and the following was determined:

1. The presence of turbidity indicated growth; the absence of turbidity indicated inhibition of growth.
2. For any extract, a result was valid only if there was turbidity (i.e. growth) in the Tube GC, and no turbidity in the Tube NC (i.e. no growth).
3. The MIC was determined as the last tube in the series (i.e. the most diluted tube) with no turbidity.

| Mean Inhibitory Conclusions (g/ml) | | | |
|---|---|---|---|
| | EtOH | MeOH | EtAc |
| *C. albicans* | 1000 | 250-1000 | >2000 |
| *A. niger* | 1000-2000 | 1000-2000 | >2000 |
| *T. mentagr.* | ≦7.56 | ≦7.56 | 250-1000 |
| *S. aureus* | 31.25-62.50 | 31.25-62.50 | 1000-2000 |
| *E. coli* | 250 | 62.50-250 | >2000 |

Results of the Experiment

From the foregoing experiment, the following results were achieved:

1. Results indicated that the ethanol and methanol *Morinda citrifolia* extracts had meaningful activity against all of the microorganisms tested.
2. Preliminary drying studies indicated that the activity using the ethanol and methanol extracts was in the 5-10 mg/ml range.
3. Ethyl acetate extracts contained <10% of the amount found in the ethanol and methanol extracts.

In conclusion, this study-clearly established antifungal activity of specific *Morinda citrifolia* fruit juice extracts. The extracts contain hundreds of compounds, and at 1000 l/ml, there may be 100 compounds at concentrations of 10 l/ml each. Thus, since the extracts tested were not purified antimicrobial compounds, even very high MIC's may be meaningful.

The present invention may be embodied in other specific forms without departing from its spirit of essential characteristics. The described embodiments are to be considered in all respects only al illustrative and not restrictive. The scope of the invention is, therefore, indicated by the appended claims, rather than by the foregoing description. All changes that come within the meaning and range of equivalency of the claims are to be embraced within their scope

What is claimed and desired to be secured by Letters Patent is:

1. A formulation for treating Candidiasis comprising: processed *Morinda citrifolia* juice;
   between about 0.1-30 percent by weight of the formulation of *Morinda citrifolia* oil; and
   between about 0.1 and 20 percent by weight of the formulation of Quercetin.

2. The formulation of claim 1, wherein said processed *Morinda citrifolia* product comprises between about 50-99.8 by weight of *Morinda citrifolia* fruit juice.

3. The formulation of claim 1, wherein said formulation further comprises *Morinda citrifolia* puree juice.

4. The formulation of claim 1, wherein said further comprises *Morinda citrifolia* puree juice concentrate.

5. The formulation of claim 1, wherein said formulation further comprises *Morinda citrifolia* fruit juice concentrate.

6. The formulation of claim 1, wherein said formulation further comprises *Morinda citrifolia* dietary fiber.

7. The formulation of claim 1, wherein said Quercetin is present in an amount between about 0.1 and 10 percent by weight of the formulation.

8. The formulation of claim 7, wherein said formulation further comprises Rutin.

9. The formulation of claim 8, wherein said Rutin is present in an amount between about 0.1 and 10 percent by weight of the formulation.

10. The formulation of claim 1 wherein said formulation is in a form suitable for oral administration.

11. The formulation of claim 1 wherein said formulation is in a form suitable for transdermal administration.

12. The formulation of claim 1, wherein said formulation is in a form suitable for intravenous administration.

13. The formulation of claim 1, wherein said formulation is in a form suitable for systemic administration.

* * * * *